United States Patent [19]
Lattner et al.

[11] Patent Number: 5,569,804
[45] Date of Patent: Oct. 29, 1996

[54] METHOD TO RECOVER CYCLIC DIOLEFIN MONOMER FROM ITS DIMER IN THE PRODUCTION OF ALKENYL BRIDGED RING COMPOUNDS

[75] Inventors: James R. Lattner, Seabrook, Tex.; Leonel E. Sanchez, Guatemala, Guatemala

[73] Assignee: Exxon Chemical Patents Inc (ECPI), Wilmington, Del.

[21] Appl. No.: 175,443

[22] Filed: Dec. 30, 1993

[51] Int. Cl.$^6$ .................................. C07C 2/50; C07C 7/00
[52] U.S. Cl. .......................... 585/361; 585/354; 585/362; 585/366; 585/800; 585/905
[58] Field of Search ..................................... 585/905, 354, 585/361, 362, 366, 800

[56] References Cited

U.S. PATENT DOCUMENTS

| | | | |
|---|---|---|---|
| 3,590,089 | 6/1971 | Robota | 260/666 |
| 3,728,406 | 4/1973 | Vrinssen et al. | 260/666 Y |
| 3,922,317 | 11/1975 | Jhawar | 260/668 |

Primary Examiner—Asok Pal
Assistant Examiner—E. D. Irzinski
Attorney, Agent, or Firm—James A. Zboray; Linda K. Russell

[57] ABSTRACT

The present invention relates to a method for using a single distillation column to recover the reactants and products from the reaction of a cyclic diolefin and an olefin to produce an alkenyl bridged ring compound.

32 Claims, 2 Drawing Sheets

METHOD TO RECOVER CYCLIC DIOLEFIN MONOMER FROM ITS DIMER IN THE PRODUCTION OF ALKENYL BRIDGED RING COMPOUNDS

FIELD OF THE INVENTION

The present invention relates to an improved process for recovering alkenyl bridged ring compounds produced by reacting olefins with cyclic diolefins and for recovering and using the unreacted cyclic diolefins to produce additional amounts of the alkenyl bridged ring compounds. More particularly, the present invention relates to an improved process for recovering 5-vinyl-2-norbornene produced by reacting butadiene with 1,3-cyclopentadiene and/or dicyclopentadiene, and for recovering and recycling the unreacted 1,3-cyclopentadiene to produce additional amounts of the 5-vinyl-2-norbornene.

BACKGROUND OF THE INVENTION

One way to produce an alkenyl bridged ring compound is to use a Diels-Alder reaction, which is the additive reaction of an olefin with a cyclic diolefin. For example, 5-vinyl-2-norbornene (an alkenyl bridged ring compound) may be produced by the Diels-Alder reaction of 1,3 butadiene (an olefin) with 1,3-cyclopentadiene (a cyclic diolefin). 5-vinyl-2-norbornene (VNB) is very desirable as it is an intermediate in the production of 5-ethylidene-2-norbornene (ENB), a termonomer used in the production of ethylene-propylene-diene monomer (EPDM) rubbers.

The conditions necessary to bring about the Diels-Alder reaction of 1,3-butadiene (BD) with 1,3-cyclopentadiene (CPD) are well known in the art. In particular, BD may be contacted with CPD in the liquid phase at temperatures of from 100° to 200° C. and a pressure of from 150 to 300 psi (1,034–2,068 kPa). It is not necessary to use a catalyst to advance the Diels-Alder reaction. The reaction is generally completed in 0.1 to 100 hours and is usually conducted under an inert atmosphere. Preferably, the reaction may be conducted in a liquid state, most preferably in a liquid-full reaction vessel.

When making VNB the preferred reaction occurs between BD and CPD, however, undesirable polymerization reactions may also occur. For example, BD monomers may react with each other to form polymers. Similar polymerization reactions may occur between CPD monomers. Undesirable by-products include dimerization of BD to form 4:vinyl-1-cyclohexene (VCH), rearrangement of VNB to form 4, 7, 8, 9-tetrahydroindene (THI) and Diels-Alder adducts of BD or CPD with VNB, VCH, or THI (hereinafter referred to as "trimers of BD/CPD").

CPD will readily react with itself to form dicyclopentadiene (DCPD). In turn, DCPD will crack upon heating, back to the CPD monomer. Therefore, both CPD and/or DCPD can be used as the cyclic diolefin feedstock in the production of alkenyl bridged ring compounds. As used herein, the term "(di)cyclopentadiene" refers to cyclopentadiene, dicyclopentadiene or mixtures thereof in the reaction mixture. In the present application, cyclopentadiene and dicyclopentadiene are regarded as the same substance in the calculation of the conversion of raw materials and, hence, the transformation of cyclopentadiene into dicyclopentadiene, and vice versa is not considered a conversion.

Certain compounds are known which suppress or inhibit the undesired polymerization reactions. Any one or combination of these inhibitor compounds may be added to the reactants in order to produce more VNB from the same amount of starting material and to avoid plugging certain parts of the reaction apparatus with the high molecular weight polymers which might otherwise be formed. Many inhibitor compounds are known in the art including 2,6-di-t-butyl-p-cresol, diphenyinitrosamine, and N-substituted p-phenylenediamines.

In addition to the problems caused by fouling, the undesired by-products are difficult to separate from VNB which create additional problems in the production process of making VNB.

As taught by U.S. Pat. No. 3,728,406, improved selectivity during the production of VNB, or any alkenyl bridged ring compounds, can be achieved by two methods. First, the starting material may be limited to the CPD monomer, rather than the DCPD dimer. This results in higher conversion of the (di)cyclopentadiene to VNB. Second, the reaction can be discontinued early after only a relatively small portion of the total CPD and/or DCPD has been consumed. One of the disadvantages of this process is that a substantial amount of residual DCPD is left in the reactor effluent. However, this residual DCPD can be recovered to produce additional alkenyl bridged ring compound. Steps to recover the DCPD include: (1) vacuum distillation to separate the DCPD from the THI and trimers of BD/CPD, or (2) selectively cracking the DCPD to CPD, which is then easily separated from the THI and trimers of BD/CPD because it is much more volatile. Unfortunately, either method requires additional processing equipment and the conditions used to crack DCPD typically result in fouling of the equipment.

It would be advantageous if a simple and economical method could be devised to recover the residual dimer of the cyclic diolefin from the production of an alkenyl bridged ring compound, by cracking the dimer to cyclic diolefin monomer, and recycle the monomer to produce more of the desired alkenyl bridged ring compound without fouling of the equipment.

SUMMARY OF THE INVENTION

The present invention relates to a continuous process which utilizes a single process step to recover the reactants and products from the Diels-Alder reaction of a cyclic diolefin and an olefin to produce an alkenyl bridged ring compound. The single process step utilizes a distillation column, to which the reaction effluent is fed. The unreacted cyclic diolefin and olefin are removed from the column as overhead products and recycled to the reaction feed mixture to produce additional alkenyl bridged ring compound. The alkenyl bridged ring compound is removed as a side stream at a location below the feel to the column, which can then be purified further by conventional means. The higher boiling reaction by-products and dimer of the cyclic diolefin are treated in the bottom of the column, such that the dimer of the cyclic diolefin is selectively "cracked", or converted back to the monomer, which then travels to the top of the column and is recovered with the recycle stream to the reaction feed mixture.

Features of this invention are that the desired alkenyl bridged ring compound is separated from both the monomer and dimer of the unconverted cyclic diolefin feed, while at the same time the dimer of the cyclic diolefin is separated from the heavy reaction by-products by conversion to the cyclic diolefin monomer. The cyclic diolefin monomer from both the reaction effluent, as well as that converted from the dimer, are simultaneously recovered in the present invention for recycle to the reaction feed mixture. Additional alkenyl bridged ring compound can then be produced from this recovered cyclic diolefin monomer.

DETAILED DESCRIPTION OF THE INVENTION

Although the foregoing and following description often refers to the separation of reactants and products from the production of VNB, the invention is not limited to such use. The present invention may be used for producing any alkenyl bridged ring compound made from a Diels-Alder reaction of a cyclic diolefin, such as CPD and/or DCPD or methyl cyclopentadiene and/or di-methyl-cyclopentadiene, with an olefin, such as ethylene, acetylene, propylene, 1,3-butadiene, 1,2-butadiene, piperylene, isoprene, etc.

Figure 1:
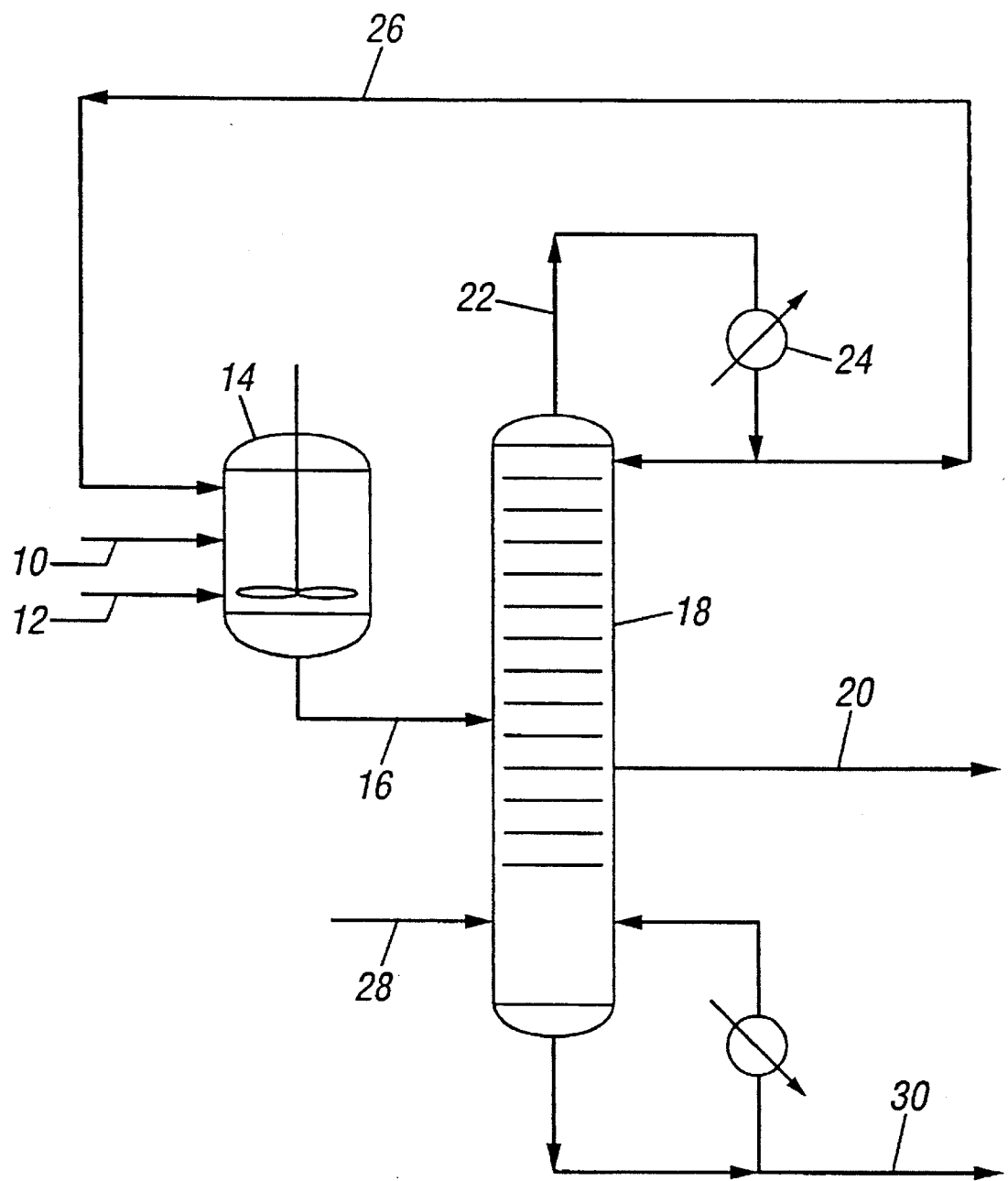
FIG. 1 is a schematic diagram which illustrates the equipment and the flow of the process used in the present invention.

Referring now to FIG. 1, in order to produce VNB, BD and (di)cyclopentadiene are fed via lines 10 and 12, respectively, into a Diels-Alder reactor 14 and reacted using known methods. Preferably the reaction is stopped when about 50 percent of the (di)cyclopentadiene feed has been converted, as described in U.S. Pat. No. 3,728,406. As noted in U.S. Pat. No. 3,728,406, the reaction time required to reach the desired degree of conversion of 50 percent or lower of the (di)cyclopentadiene will vary according to reaction conditions such as temperature, pressure, ratio of reactants, presence and amount of catalyst, if any, etc. Thus, no absolute reaction times can be set forth. However, one skilled in the art easily should be able to determine the necessary reaction time by performing an orienting experiment using a given set of reaction conditions. Generally, reaction times should be less than one hour but greater than ten minutes.

Once the reaction has reached the desired conversion level, the effluent from the Diels-Alder reactor may be fed via line 16 to a distillation column 18. The effluent should contain BD, CPD, diluent (typically a C6-C7 aliphatic or aromatic solvent), VCH, VNB, THI, DCPD, and trimers of BD and CPD.

The distillation column 18 should be maintained at an operating pressure of between about 5–30 psia (34.4–206.8 kPa), preferably between about 11–17 psia (75.8–117.2 kPa). Higher pressures result in unacceptable levels of conversion of VNB to THI and an increased potential to foul the column reboiler. Lower pressures would result in column temperatures which would be insufficient to achieve significant cracking of DCPD to CPD. The temperature in the bottom of the column should be maintained at least above about 130° C. (266° F.), preferably between about 170°–190° C. (338°–374° F.), and more preferably about 175° C. (347° F.).

The crude VNB, which also includes some VCH, THI, and DCPD, is removed from the column, preferably in a side stream via line 20, which should be located at a point below the feed. The removal of VNB as a side stream, rather than leaving the VNB in the bottoms, minimizes the undesired conversion of VNB to THI. The VNB side stream subsequently is treated with additional distillation steps (not shown), using known procedures, to remove the lighter boiling VCH and the heavier-boiling THI and DCPD.

Under the foregoing column conditions, the lighter boiling BD and CPD from the effluent travels up the distillation column, along with the light boiling diluent, and may be removed as overhead via line 22 and recycled to the Diels-Alder reactor 14, e.g., via a heat exchanger 24 and recycling line 26.

The remaining bottoms should contain primarily THI, DCPD, and trimers of BD/CPD and other oligimers of CPD, BD, and acyclics. The bottoms may be left in the distillation column, or otherwise exposed to the foregoing column conditions, for at least fifteen minutes, preferably at least one hour, during which time approximately 90% of the DCPD in the bottoms will crack to monomeric CPD. The resulting CPD will travel up the column and may be removed as overhead via line 22 and recycled to produce additional VNB.

The resulting DCPD-depleted heavy product may be removed as bottoms via line 30.

One surprising result when the bottoms is left in the column for at least fifteen minutes to crack the residual DCPD is the very low polymer formation or fouling of the equipment. The literature teaches that, when trying to crack DCPD to CPD in the liquid phase, it is essential to use a high-boiling inert solvent to minimize the formation of CPD oligomers which foul the equipment. See U.S. Pat. No. 3,590,089, incorporated herein by reference. No such solvent is added to the bottoms during cracking according to the present invention. Therefore, without limiting the invention to any particular theory, it appears that the THI and trimers of BD/CPD in the bottoms behave as diluents in the cracking reaction. This result is unexpected since these trimers are not inert to additional thermal Diels-Alder reactions. Nevertheless, analysis of the reboiler heat transfer coefficient during extended runs show that the coefficient holds fairly stable. Visual inspection of the reboiler following the total period of the run showed only a very thin film of polymer on the heat transfer surfaces. No polymer collected on the filters in the bottoms product effluent line.

Another surprising result when the bottoms is cracked is the very high DCPD cracking level achieved (approximately 90%) in the boiling liquid of the column bottoms at atmospheric pressure and at a temperature as low as 175° C. (347° F.). Again, without limiting the present invention to any particular theory, it appears that the presence of high-boiling trimers of BD/CPD in the bottoms is necessary to achieve the desired cracking levels without the external addition of a high boiling solvent.

The "in column" cracking of DCPD in the present invention can result in two additional benefits. First, the fresh make-up DCPD may be passed through the distillation column 18, e.g., via line 28, before being fed to the Diels-Alder reactor. This allows virtually all of the (di)cyclopentadiene feed to the Diels-Alder reactor to be monomeric CPD, rather than a mixture of CPD and DCPD. Second, when further purification of the crude VNB takes place, the portion of the VNB side stream containing DCPD can be returned to the bottoms in the distillation column 18 for cracking according to the present invention.

EXAMPLE

This process was demonstrated as described below in a continuous pilot unit for 6 weeks.

13.0 lb/hr BD and 13.2 lb/hr (di)cyclopentadiene (mostly CPD) and 14.1 lb/hr of toluene (a diluent) were fed into a Diels-Alder reactor and reacted in order to produce VNB.

The reactor was operated at a temperature of 154° C. (310° F.) and at a pressure of 300 psi (2,067 kPa) to keep all reactants in the liquid phase. The residence time of the reactor was one hour, which resulted in a 33% conversion of the (di)cyclopentadiene.

The effluent from the Diels-Alder reactor was fed to a distillation column. The effluent contained BD, CPD, toluene, VCH, VNB, THI, DCPD, and trimers of BD/CPD.

The distillation column was maintained at an operating pressure of 12 psia (83 kPa). The temperature in the bottom of the column was maintained at about 175° C. (347° F.). The column had an internal diameter of 6 inches, and contained 60 feet of woven wire mesh packing.

The lighter boiling BD and CPD, along with the toluene, was removed as overhead and recycled to the Diels-Alder reactor via a heat exchanger and recycling line. The VNB was removed as a side-stream, along, with the VCH and with a small amount of CPD, THI, DCPD, and heavy by-products.

The remaining bottoms contained primarily THI, DCPD, and trimers and other oligimers of CPD, BD, and acyclics, most of which contained fourteen carbon atoms and were comprised of two CPD monomers and one BD monomer. The bottom were exposed to the foregoing column conditions for 2 hours during which time approximately 90% of the DCPD in the bottoms cracked to monomeric CPD. The resulting CPD was removed as overhead and recycled to produce additional VNB.

The resulting DCPD-depleted heavy product was removed as a bottoms steam.

The presence of fouling in the heat exchanger providing heat for both the distillation and the cracking of DCPD to CPD was determined by calculating the heat transfer coefficient:

$$\text{Heat transfer coefficient } \text{Btu/hr ft}^2 \text{ °F.} = \frac{(\text{Heat exchanged, Btu/hour})}{(\text{exchanger surface area ft2}) \times (\text{steam temp-process temp, °F.})}$$

Figure 2:
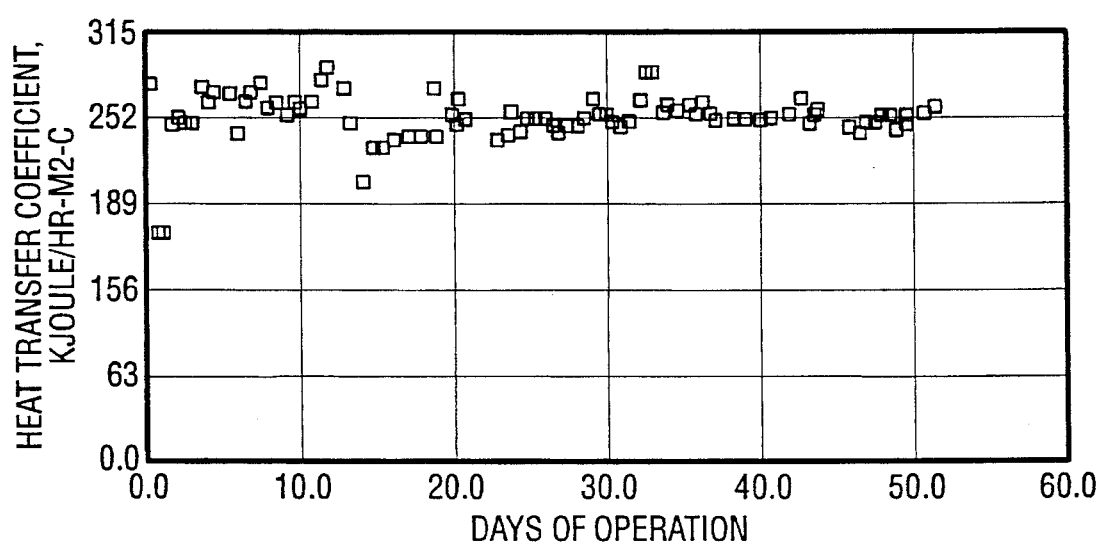
FIG. 2 is a graph of heat transfer coefficient of the heat exchanger used in the Example.

This data is plotted in the FIG. 2, and shows no decline in heat transfer coefficient over the duration of the run. This is an indication that fouling is not a problem.

Visual inspection of the reboiler following the total period of the run showed only a very thin film of polymer on the heat transfer surfaces. No polymer collected on the filters in the bottoms product effluent line.

One of skill in the art will appreciate that many modifications may be made to the embodiments described herein and explained in the accompanying figure without departing from the spirit of the present invention. Accordingly, the embodiments described herein are illustrative only and are not intended to limit the scope of the present invention.

I claim:

1. A method for using a single distillation column to recover the reactants and products from the reaction of a cyclic diolefin and an olefin to produce an alkenyl bridged ring compound comprising:
   (a) feeding an effluent from the reaction of said cyclic diolefin with said olefin to a distillation column;
   (b) removing said alkenyl bridged ring compound from said distillation column as a side stream at a location below said effluent feed;
   (c) removing an overhead from said column comprising said cyclic diolefin, predominantly in monomeric form, leaving a bottoms comprising said cyclic diolefin, predominantly in dimerized form, and heavy byproduct; and
   (d) cracking the dimerized cyclic diolefin in said bottoms whereby additional monomeric cyclic diolefin is recovered.

2. The method of claim 1, wherein said bottoms is cracked for at least fifteen minutes at a temperature above about 130° C. (266° F.) and at a pressure between about 5–30 psia (3.5–206.8 kPa).

3. The method of claim 2, wherein said bottoms is cracked for at least one hour.

4. The method of claim 1, wherein said cyclic diolefin is selected from the group consisting of 1-methyl-1,3-cyclopentadiene, 2-methyl-1,3-cyclopentadiene, 5-methyl-1,3-cyclopentadiene, or mixtures thereof.

5. The method of claim 1, wherein said cyclic diolefin is 1,3-cyclopentadiene, said olefin is butadiene, and said alkenyl bridged ring compound is 5-vinyl-2-norbornene.

6. The method of claim 5, wherein said bottoms is cracked for at least fifteen minutes at a temperature above about 130° C. (266° F.) and at a pressure between about 5–30 psia (34.5–206.8 kPa).

7. The method of claim 6, wherein said bottoms is cracked for at least one hour.

8. The method of claim 6, wherein said bottoms is cracked at a pressure between about 11–17 psia (75.8–117.2 kPa).

9. The method of claim 6, wherein said bottoms is cracked at a temperature of about 170°–190° C. (338°–374° F.).

10. The method of claim 8, wherein said bottoms is cracked at a temperature of about 170°–190° C. (338°–374° F.).

11. The method of claim 1, further comprising the step of reacting said additional monomeric cyclic diolefin with said olefin to form additional alkenyl bridged ring compound.

12. The method of claim 2, further comprising the step of reacting said additional monomeric cyclic diolefin with said olefin to form additional alkenyl bridged ring compound.

13. The method of claim 3, further comprising the step of reacting said additional monomeric cyclic diolefin with said olefin to form additional alkenyl bridged ring compound.

14. The method of claim 5, further comprising the step of reacting said additional 1,3-cyclopentadiene with said butadiene to form additional 5-vinyl-2-norbornene.

15. The method of claim 6, further comprising the step of reacting said additional 1,3-cyclopentadiene with said butadiene to form additional 5-vinyl-2-norbornene.

16. The method of claim 9, further comprising the step of reacting said additional 1,3-cyclopentadiene with said butadiene to form additional 5-vinyl-2-norbornene.

17. The method of claim 1, further comprising feeding a stream of the dimer of said cyclic diolefin to said distillation column.

18. The method of claim 2, further comprising feeding a stream of the dimer of said cyclic diolefin to said distillation column.

19. The method of claim 3, further comprising feeding a stream of the dimer of said cyclic diolefin to said distillation column.

20. The method of claim 5, further comprising feeding a stream of the dimer of said 1,3-cyclopentadiene to said distillation column.

21. The method of claim 6, further comprising feeding a stream of the dimer of said 1,3-cyclopentadiene to said distillation column.

22. The method of claim 7, further comprising feeding the stream of the dimmer of said 1,3-cyclopentadiene to said distillation column.

23. The method of claim 9, further comprising feeding a stream of the dimer of said 1,3-cyclopentadiene to the said distillation column.

24. An improved method for recovering reactants and products from the production of 5-vinyl-2-norbornene comprising:

(a) reacting 1,3-butadiene with a 1,3-cyclopentadiene or dicyclopentadiene feed to form an effluent;

(b) feeding said effluent to a distillation column;

(c) removing 5-vinyl-2-norbornene from said distillation column as a side stream at a location below said effluent feed;

(d) removing an overhead comprising 1,3-cyclopentadiene from said column, leaving a bottoms comprising dicyclopentadiene and heavy byproduct;

(e) cracking said bottoms in said column for at least one hour at a temperature of about 175° C. (347° F.) at a pressure between about 11–17 psia (75.8–117.2 kPa) to form additional cyclopentadiene; and (f) recovering said additional 1,3-cyclopentadiene.

25. The method of claim 24, further comprising the step of reacting said additional cyclopentadiene with said butadiene to form additional 5-vinyl-2-norbornene.

26. The method of claim 24, further comprising the step of cracking at least a portion of said cyclopentadiene feed along with said bottoms before reacting said cyclopentadiene with said butadiene to form said 5-vinyl-2-norbornene.

27. Cyclopentadiene produced by a method comprising the following steps:

(a) reacting 1,3-butadiene with a 1,3-cyclopentadiene or dicyclopentadiene feed to form an effluent;

(b) feeding said effluent to a distillation column;

(c) removing 5-vinyl-2-norbornene from said distillation column as a side stream at a location below said effluent feed;

(d) removing an overhead comprising cyclopentadiene from said column, leaving a bottoms comprising dicyclopentadiene and heavy byproduct;

(e) cracking said bottoms for at least fifteen minutes at a temperature above about 130° C. (266° F.) at a pressure between about 5–30 psia (34.4–206.8 kPa) to form additional cyclopentadiene; and (f) recovering said additional cyclopentadiene without removing said bottoms from said column.

28. The product of claim 27, wherein said bottoms is cracked in said column for at least 15 minutes.

29. The product of claim 28, wherein said bottoms is cracked at a pressure between about 11–17 psia (75.8–117.2 kPa) and at a temperature of about 175° C. (347° F.).

30. 5-vinyl-2-norbornene produced by a method comprising the steps of:

(a) reacting butadiene with a cyclopentadiene feed to form an effluent;

(b) feeding said effluent to a distillation column;

(c) removing 5-vinyl-2-norbornene from said distillation column as a side stream at a location below said effluent feed;

(d) removing an overhead comprising cyclopentadiene from said column, leaving a bottoms comprising dicyclopentadiene and heavy byproduct;

(e) cracking said dicyclopentadiene for at least fifteen minutes at approximately 175° C. (347° F.) at a pressure between about 11–17 psia (75.8–117.2 kPa) to form additional cyclopentadiene;

(f) recovering said additional cyclopentadiene.

31. 5-vinyl-2-norbornene produced by the method of claim 30, wherein at least part of said cyclopentadiene feed has been cracked along with said bottoms.

32. 5-vinyl-2-norbornene produced by the method of claim 31, wherein at least part of said cyclopentadiene feed has been cracked along with the bottoms.

\* \* \* \* \*